United States Patent [19]

Bolon

[11] Patent Number: 4,670,656
[45] Date of Patent: Jun. 2, 1987

[54] PROCESS AND APPARATUS FOR MEASURING SURFACE DISTRIBUTIONS OF CHARGED PARTICLE EMITTING RADIONUCLIDES

[75] Inventor: Craig Bolon, Brookline, Mass.

[73] Assignee: Betagen Corporation, Cambridge, Mass.

[21] Appl. No.: 560,960

[22] Filed: Dec. 13, 1983

[51] Int. Cl.$^4$ ............................................. G01T 1/185
[52] U.S. Cl. .................................... 250/385; 250/374
[58] Field of Search ........... 250/385, 374, 388, 390 R, 250/375, 361 R

[56] References Cited

U.S. PATENT DOCUMENTS

| | | | |
|---|---|---|---|
| 3,772,521 | 11/1973 | Perez-Mendez | 250/385 |
| 3,786,270 | 1/1974 | Borkowski et al. | 250/385 |
| 3,898,465 | 8/1975 | Zaklad et al. | 250/389 |
| 3,942,012 | 3/1976 | Boux | 250/385 |
| 4,019,057 | 4/1977 | Bram | 250/375 |
| 4,264,816 | 4/1981 | Walenta | 250/374 |
| 4,286,158 | 8/1981 | Charpak et al. | 250/374 |
| 4,320,299 | 3/1982 | Bateman et al. | 250/374 |

FOREIGN PATENT DOCUMENTS 874721 8/1961 United Kingdom ................ 250/385

OTHER PUBLICATIONS

Article entitled The Use of Multiwire Proportional Counters to Select and Localize Charged Particles by G. Charpak, R. Bouclier, T. Bressani, J. Favier and C. Zupancic, Cern, Geneva, Switzerland, Nuclear Instruments and Methods 62 (1968), 262-268; North-Holland Publishing Co.
Article entitled Some Read-Out Systems for Proportional Multiwire Chambers, G. Charpak, R. Bouclier, T. Bressani, J. Favier and C. Zupancic, Cern Geneva, Switzerland, Nuclear Instruments and Methods 65 (1968), 217-220; North-Holland Publishing Co.
Article entitled Some Developments in the Operation of Multiwire Proportional Chambers, G. Charpak, D. Rahm and H. Steiner, Cern, Geneva, Switzerland, Nuclear Instruments and Methods 80 (1970), 13-34; North-Holland Publishing Co.
Article entitled Signal, Noise and Resolution in Position-Sensitive Detectors V. Radeka, published in IEEE Transactions on Nuclear Science, vol. NS-21, No. 1, pp. 51-64 (Feb., 1974).
Article entitled Use of a Proportional Chamber for Quantitative and Qualitative Analysis of Thin-Layer Radiochromatograms, Yu. V. Zanevsky, S. P. Chernenko, A. B. Ivanov, L. B. Kaminir, V. D. Peshekhonov, E. P. Senchenkov, I. A. Tyapkin and V. N. Kalinin, High Energy Laboratory, Joint Institute for Nuclear Research, Dubna, U.S.S.R., Nuclear Instruments and Methods 153 (1978), 445-447; North-Holland Publishing Co.
Article entitled A Beta-Ray Imaging Device for Radiochromatography, Hoan Nguyen NGOC, Jack Jeanjean and Pierre Desaunais, Laboratoire de l'Accelerateur Lineaire, 91405 Orsay Cedes, France, Nuclear Instruments and Methods 173 (1980), 605-607, North-Holland Publishing Company.
Article entitled The Multistep Avalanche Chamber as a Detector in Radiochromatography Imaging, G. Petersen, the Niels Bohr Institute, University of Copenhagen, Copenhagen, Denmark, G. Charpak, G. Melchart and F. Sauli, Cern, Geneva, Switzerland, Nuclear Instrument and Methods 176 (1980), 239-244; North-Holland Publishing Company.

(List continued on next page.)

*Primary Examiner*—Carolyn E. Fields
*Attorney, Agent, or Firm*—Lahive & Cockfield

[57] ABSTRACT

A process for precision measurement of charged particle emissions from a surface and an apparatus for providing a high resolution digital image of the distribution of such emissions in a minimum exposure time over a relatively large surface area. The process of measurement uses the direction of emissions as determined by two or more position measuring elements of an area detector. The apparatus is based on multiple region detector elements that employ proportional amplification of ionization in a gas.

40 Claims, 9 Drawing Figures

OTHER PUBLICATIONS

Article entitled An Efficient Two-Dimensional Scanner for Beta Emitters, R. G. Markham, Sam M. Austin, Cyclotron Laboratory and Physics Department, Michigan State University, East Lansing, MI 48824, and M. Stya, Cyclotron Laboratory and MSU-DOE Plant Research Laboratory, Michigan State University, East Lansing, MI 48824, Nuclear Instruments and Methods 160 (1979), 49-53; North-Holland Publishing Co.

Article entitled A Simple Electronic Apparatus for the Analysis of Radioactively Labeled Gel Electrophoretograms, Konstantin Goulianos, Karen Kaye Smith, and Sebastian N. White, the Rockefeller University, New York, New York 10021, Analytical Biochemistry 103, 64-69 (1980).

Article entitled Linear Analyzer Improves Detection in Radio-TLC Tests by H. Filthuth, Laboratorium Prof. Dr. Berthold, reprinted from Industrial Research & Development, Jun. 1981.

Catalog entitled High Resolution Radioisotope Camera 450-4 (Spark Chamber) by Birchover Instruments Ltd.; undated.

Catalog entitled Radiochromatogramme Static Radiochromatogram Reader by Numelec Sein; undated.

Untitled paper distributed by Bioscan, Inc., as part of Catalog for BID System 100, by Seth D. Shulman, President-Bioscan, Dec., 1980.

Catalog entitled Berthold TLC Linear Analyzer LB 282, LB 283 by Beta Anaytical, Inc.; undated.

Catalog entitled Beta Spark Camera LB 291 for Short-Time Imaging of Radioactivity Distribution in TLC Plates; undated.

Catalog entitled 2-D-TLC-Scanner LB 276 by Beta Analytical, Inc., undated.

PROCESS AND APPARATUS FOR MEASURING SURFACE DISTRIBUTIONS OF CHARGED PARTICLE EMITTING RADIONUCLIDES

BACKGROUND OF THE INVENTION

This invention concerns, generally, a system for measuring the spatial distribution of charged particle emitting radionuclides across the surface of a material and, more particularly, a process for precision measurement of charged particle emissions from a surface and an apparatus for providing a high resolution digital image of the distribution of such emissions in a minimum exposure time over a relatively large surface area.

There are several procedures in which it is necessary to measure detailed distributions of charged particle emitting radionuclides across the surface of a material. Some of these involve relatively large surface areas, up to ¼ square meter. One such procedure is mapping concentrations of phosphorus-32 labelled compounds in thin layer polyacrylamide gels. In the past, several different approaches to this measurement problem have been employed.

Autoradiography provides simultaneous, high resolution recording for a large area. However, photographic film is relatively insensitive to energetic beta emissions, has limited exposure range, must be developed and read by additional procedures, and records a background from chemical film fog and natural sources of radioactivity. Intensifying screens are used to enhance the sensitivity of photographic film, but they degrade spatial resolution.

Another approach uses scanning detectors of a variety of types, including gas ionization detectors, scintillators, and other solid state detectors. Some of these detect only a point at a time, while others simultaneously record a line or a small area. However, scanning detectors require a relatively long time to cover an area that is large compared to the sensitive area of the detector.

Segmented detectors have also been constructed, using multiples of the type of detectors employed in scanning. Both scanning and segmentation may introduce boundary effects, mechanical distortion, and artifacts in their measured distributions.

Still another approach has been large area detectors. However, high resolution solid state devices, such as multichannel plates, have proven difficult to construct in large sizes. Existing techniques involving gas ionization detectors have not been capable of providing high spatial resolution, particularly for energetic beta emissions.

It is therefore a primary objective of the present invention to provide an apparatus and a process for direct digital measurement of surface distributions of charged particle emitting radionuclides, capable of high spatial precision, resolving spots of radionuclide concentrations at very small separations.

It is another objective of the present invention to provide measurement of radionuclide distributions over large surface areas with high efficiency in detecting radioactive emissions and consequent short exposure time.

It is still another objective of the present invention to provide high resolution, large area measurements of radionuclides with energetic beta emissions, such as phosphorus-32.

It is a further objective of this invention to provide quantitative measurements of radionuclide activity with wide dynamic range, permitting the measurement of low radionuclide activity concentrations in the presence of high activity concentrations.

DESCRIPTION OF THE PRIOR ART

Several types of radioactivity detectors have been developed which are based on proportionally amplified ionization in a gas. In most of these, an arrangement of electrostatic fields causes electrons from primary ionization created by an incident event to move toward one or more fine wires or conductive fibers. A strong electrostatic field near the surface of a wire or fiber causes these primary electrons to collide vigorously with the gas atoms, knocking off additional electrons in a controlled avalanche. Electronic circuits record the resulting charge signal. It is possible to adjust conditions of operation so that signal amplitudes are proportional to amounts of primary ionization.

A multiwire proportional grid is one form of sensitive element in position measuring ionization detectors based on proportional amplification in a gas. Such a grid is an electrode consisting of uniformly spaced fine wires or conductive fibers. To make a position measuring chamber, such a grid is immersed in an appropriate gas mixture and a strong electrostatic field. An ionizing event in the chamber produces a localized cluster of primary electrons, each of which is attracted toward a wire of the proportional grid. As the electrons reach the surfaces of the wires, they produce local avalanches, yielding measurable charge signals. By identifying the wires on which signals occur, or by obtaining a positional centroid of the signals on several wires, the position of the center of the primary cluster of ionization is measured in one dimension of the grid surface. A parallel grid adjacent to a multiwire proportional grid will provide induced charge siganls through capacitive coupling. Position measurements in two dimensions can be obtained by using these induced signals on adjacent electrodes.

A useful position measuring ionization detector based on proportional amplification in a gas consists of a gas enclosure containing one or more position measuring chambers, each incorporating a multiwire proportional grid. Suitable configurations, construction materials, gas mixtures, readout methods, and operating conditions for detectors of this type are well known in the art. They are described in U.S. Pat. Nos. 3,772,521 and 3,786,270 and in the following articles:

(1) G. Charpak, R. Bouclier, T. Bressani, J. Favier, and C. Zupancic, "The use of multiwire proportional counters to select and localize charged particles," Nuclear Instruments and Methods 62:262-268 (1968).

(2) G. Charpak, R. Bouclier, T. Bressani, J. Favier, and C. Zupancic, "Some readout systems for proportional multiwire chambers," Nuclear Instruments and Methods 65:217-220 (1968).

(3) G. Charpak, D. Rahm, and H. Steiner, "Some developments in the operation of multiwire proportional chambers," Nuclear Instruments and Methods 80:13-34 (1970).

A position measuring ionization detector based on proportional amplification in a gas will be highly sensitive to radionuclide beta emissions. With appropriate readout circuitry, it can count essentially every beta emission entering its sensitive volume. However, such a detector yields poor spatial resolution for all but the lowest energy emissions. This is because energetic betas travel a long distance through a gas, leaving an extended track of ionization along their paths. A planar multiwire proportional chamber will make severe parallax errors when measuring emission paths at a large angle with respect to the normal to its grid.

One attempt to cope with this problem has been the multistep avalanche chamber. This adds to a multiwire proportional chamber a gas volume with a very strong electrostatic field defined by additional electrodes parallel to the multiwire proportional grid. Avalanche multiplication of ionization occurs throughout the volume where there is a strong field, and the amplified ionization drifts through a grid or mesh electrode toward the multiwire proportional grid, where it is detected. This makes the chamber primarily sensitive to ionization created in its strong field volume near the side opposite the multiwire proportional grid. If a source surface is introduced into the detector gas in contact with the outer electrode of the strong field volume, the detector then becomes sensitive mainly to ionization occurring in a thin layer of gas adjacent to the source surface. This will reduce parallax errors.

Suitable configurations, construction materials, gas mixtures, readout methods, and operating conditions for multistep avalanche chambers have been described in the following article:

(4) G. Petersen, G. Charpak, G. Melchart, and F. Sauli, "A multistep avalanche chamber as a detector in radiochromatography imaging," Nuclear Instruments and Methods 176:239–244 (1980).

As developed so far, multistep avalanche chambers have significant limitations for recording distributions of beta emissions. They yield substantially poorer resolution for the more energetic beta emissions, because of an increased likelihood of detecting ionization in their sensitive gas layer that is far away from the emission origin. These chambers must be operated at precisely controlled field strengths, and they are therefore sensitive to electrostatic field distortions resulting from contact with or close proximity to surfaces of a source material. These chambers produce a wide range of signal amplitudes, because of large statistical variations in the very small numbers of primary electrons to which they respond. They require introduction of a potentially contaminating source material into the detector gas, while high purity of the detector gas is needed for stable operation.

SUMMARY OF THE INVENTION

A major concern when measuring the origin of an energetic charged particle emission is the extended path of the emission. The measurement process of this invention is: (1) to detect ionization along charged particle emission paths, (2) to employ detectors that can respond to emissions from a substantial area of source material surface, (3) to provide separate detector elements that measure ionization centroid coordinates of at least two points along an emission path, (4) to estimate, by means of a straight line passing through the measured points, the direction of the path, and (5) using the direction of a path, (a) to adjust the position measurement made closest to the emission origin to a projected point on the source material surface, (b) to limit emission recording to those emissions having path angles within an acceptance range, or (c) to provide both a coordinate adjustment and an acceptance criterion. A direction measurement consists of a projected angle with respect to the normal to a source material surface. Such a direction measurement, coordinate adjustment, and acceptance criterion may apply to either one or both coordinates of the source material surface.

The apparatus of this invention is a radioactive imaging device so constructed that the distribution of a charged particle emitting radionuclide at or near the surface of a source material can be obtained. It is based on a multi-chamber, gas ionization detector. The detector operates in a counting mode, recording ionization signals, obtaining from them ionization centroids for at least two points along an emission path, and estimating from these measurements the coordinates at the origin of each emission. Although most easily constructed for planar source surfaces, detectors may also be constructed for simply curved source surfaces. Such an apparatus is particularly useful for energetic beta emissions, although with low gas pressures and low density construction materials, it may also be used for other particle emissions and for low energy emissions.

A data acquisition subsystem of an apparatus constructed according to this invention obtains from the origin coordinates of many charged particle emissions a radionuclide distribution at or near the surface of a source material. It does this by counting, within spatial elements of a measurement area corresponding to the source surface, emissions whose estimated coordinates fall within the boundaries of such area elements. This may be done, for example, by utilizing a memory array or a multichannel digital counter, which may employ a digital processing system control. Each of the channels or memory locations is associated with an area element of the source material. For each emission for which the estimated origin coordinates correspond to a specific element of area, the count in the corresponding memory location or digital channel is incremented, provided that the emission angles are within an acceptable range and the emission energies are within an acceptable range. After a substantial number of emissions has been recorded, the counts in the source surface area elements indicate their respective concentrations of radionuclide.

The position measuring chambers of the detector for the apparatus are contained in a gas tight enclosure, which also provides electrical insulation and shielding. On one side, the detector enclosure has an especially thin outer wall, or window, in close proximity to or direct contact with the source material, which is to be located outside the enclosure. The function of this window is to isolate the detector from the external environment, while permitting emissions to travel from the source material into the detector with minimal absorption and scattering. The window includes an electrically conductive layer and should be made of materials with low density and atomic number.

Position measuring chambers within a detector are each composed of two or more relatively thin regions that are filled with a gas mixture and bounded by electrodes parallel to the surface of a charged particle emitting source material. If the source surface is planar, the electrodes will also be planar. Electrodes situated between regions are made of wires or conductive fibers arranged as parallel grids, crossed grids, or meshes. Such electrodes define equipotential surfaces for an electrostatic field but permit electrons moving under the influence of the field to pass from one region to another. Electrons move in a direction normal to the electrode surfaces. The outer electrodes of a chamber may be made in the same way, or they may be made of films, foils, laminates, or solid materials. These define equipotential surfaces of a field but need not permit transmission of electrons. Electrode elements may be printed, evaporated, plated, etched, or machined on such outer electrode surfaces.

The position measuring chambers in a detector will include at least one detection region. A conventional multiwire proportional chamber may be used as a position measuring chamber, consisting of two detection regions, separated by a multiwire proportional grid and bounded by outer electrodes. The function of detection regions is to measure centroid positions of small clusters of ionization deposited along segments of emission paths. Such a measurement is performed by electronic processing of charge signals from conductive elements of the electrodes bounding detection regions. Either directly or through intermediate steps, such processing yields positional centroids of the signals on electrode elements. These quantities are proportional to coordinates, parallel to the electrode surfaces, of the center of charge for an ionization cluster. The third dimension of such a measurement is provided by the location of the median surface in the region or regions from which ionization was collected.

One electrode bounding detection regions of a position measuring chamber within the apparatus is a multiwire proportional grid. The other electrodes in a chamber are at successively more negative potentials, so as to attract electrons toward this grid. At a multiwire proportional grid, amplification of ionization electrons occurs in strong electrostatic fields close to its fine wires or conductive fibers. Charge signals will be observed on the elements of a multiwire proportional grid. At least one other electrode adjacent to a multiwire proportional grid is also a parallel grid, with conductive elements oriented at an angle to those of the multiwire proportional grid or to those of another electrode adjacent to the multiwire proportional grid. Capacitive coupling will cause induced charge signals to be observed on the elements of such an adjacent grid. Signals on the elements of two grid or grid-like electrodes bounding the detection regions are processed by readout circuits to measure the centroid of a primary cluster of ionization in two dimensions.

In order to maximize spatial resolution, the apparatus is designed to measure a first point along an emission path as close as possible to the emission origin. The chamber measuring this first point will consist of multiple regions and may include up to five regions in the following order: a collection region, an amplification region, a transfer region, and two detection regions.

An amplification region of a position measuring chamber has a strong enough electrostatic field so that, as electrons move through it, they collide vigorously with gas atoms, knocking off additional electrons from gas molecules. This is the same type of amplification which occurs at a multiwire proportional grid. In an amplification region, however, this process occurs throughout a gas volume rather than being confined to the immediate vicinity of an electrode surface. Depending on the gas mixture and the details of chamber construction, stable amplification factors of up to about 10,000 can be obtained for primary ionization electrons completely traversing an amplification region. The amplification for a primary electron varies exponentially with the thickness of amplification region that it traverses.

The main function of an amplification region is to separate ionization originating on one side of the region from ionization deposited elsewhere in the chamber. Electrons entering from the side at the more negative potential will receive full amplification, while electrons originating only slightly beyond this boundary will receive much less amplification. Detection regions on the more positive side of an amplification region will respond almost entirely to ionization electrons thus amplified. On the more negative side of an amplification region, a collection region may be added to define the thickness of gas within which a position measuring chamber with an amplification region will respond to primary ionization.

The main function of a collection region is to provide a gas layer of small, controlled thickness within which primary ionization is collected to measure a point on a path. Such a region will be thick enough to contain an average of a few primary ionization electrons along a path. By providing a controlled ionization sample and by creating electrostatic isolation from deformations of the detector window, a collection region stabilizes the detector's signal amplitudes and spatial resolution. The minimum useful thickness of a collection region is determined by ionization statistics in the detector gas. For beta emissions of 0.3 MeV or more and a typical gas at atmospheric pressure, this will be around 1 mm. Additional thickness is undesirable, because it will reduce spatial resolution. A moderate electric field will sweep ionization from a collection region through a grid or mesh electrode into an amplification region.

A transfer region is an optional gap of variable thickness between an amplification region and the nearest detection region. A moderate electrostatic field, comparable to that in the collection region, sweeps ionization through the transfer region into the detection regions. A transfer region isolates an avalanche region electrostatically from detection regions and acts as an inhibitor of stray secondary amplification. Only a fraction of the ionization from the amplification region enters a transfer region, as controlled by the ratio of the transfer region field to the amplification region field. A flow of positive ions from detection regions, moving toward the amplification region, is similarly controlled by the ratio of transfer region field to detection region field.

The second position measuring chamber in the detector may be a conventional multiwire proportional chamber, with two detection regions separated by a multiwire proportional grid. It may also include additional electrodes and regions, like the first chamber. The function of the second chamber in the detector is to measure the coordinates of a second point on an emission path. With this information, the apparatus can obtain projected angles of a path with respect to the normal to detector surfaces, in either or both of two dimensions parallel to the surfaces. The coordinates obtained from the first chamber are adjusted by a simple formula, projecting an assumed straight line path to the surface of the source material, to estimate the coordinates of an emission origin. This calculation can readily be performed at speeds fast enough for practical applications by analog or digital electronic circuits. It is possible to incorporate additional chambers in a detector, providing more points along a path. However, for most applications, these would add complexity without significantly improving spatial resolution.

The spatial resolution of a detector of the type outlined is strongly affected by scattering of emissions within the detector. As a charged particle passes through the chamber gas and the electrode materials, its path is deflected in a statistical manner, according to well understood physical principles. This scattering can cause significant errors in the estimation of emission coordinates and angles. Because of this behavior, it is advantageous to construct electrodes of thin materials with low density and atomic number.

The effects of scattering on spatial resolution increase rapidly at large emission angles with respect to the normal to the source surface and at low emission energies. The energies of charged particle emissions from radionuclides are distributed in a well understood way over a range extending from zero to a maximum energy. Because of this distribution, some emissions from all radionuclides will be at low energies. These factors make it advantageous to reject—that is, to omit counting—emissions at large emission angles and at low emission energies.

Path angle information provided by the process and apparatus of this invention can be used to reject wide angle emissions. As a range of accepted angles is constrained, spatial resolution will improve at a cost in sensitivity. It is possible to predict detector behavior from physical principles and to optimize an angular acceptance criterion for a particular application.

The amounts of primary ionization along emission paths do not vary significantly for most emission energy ranges of practical interest, so that signal amplitudes from the detector will not provide useful energy information. However, the detector can be adapted for the emission energy distribution of a particular radionuclide by including a plate of absorbing material. Such a material should be low in atomic number, so that it does not produce energetic x-ray fluorescence. It may also be constructed in layers of different materials, to provide additional reduction of fluorescence. Charged particle emissions below a fairly well defined threshold energy will not penetrate such an absorber, hence will not be detected in a chamber that follows the absorbing plate.

When using an absorber, there will be substantial scattering in the absorber for emissions that penetrate it. Because of this, it will be necessary to measure the second point on a path either ahead of the absorber or as close to it as possible. Either of two methods can be used: (1) measure a coordinate ahead of an absorber and introduce a third chamber after the absorber, simply to record the presence or absence of an emission path beyond the absorber, or (2) make a second chamber of the same configuration as the first, with its collection region immediately following the absorber plate.

An alternative method for energy discrimination is to include, following the second position measuring chamber in a detector, a plate of scintillator material, of such a composition and thickness that emissions at all energies produced by the source radionuclide will be completely absorbed. This scintillator will be viewed by a phototransducer which provides an electrical signal whose amplitude is proportional to the amount of light reaching it. From the amplitude of the phototransducer signal, the energy of an emission can be estimated. Emissions whose energies fall below a threshold energy can then be rejected.

For weak radionuclide concentrations, cosmic rays and other natural sources of radioactivity can add significant background to a measured radionuclide distribution. Some of the background events, such as those caused by cosmic ray muons, will produce a detector response that is indistinguishable from that for energetic beta emissions. It some situations, it may be desirable to suppress this background.

Background counts can be suppressed by placing one or more additional multiwire proportional counters or scintillation counters following an optional plate of absorber material, sufficiently thick that no emission from the source material can penetrate it, either (1) on the opposite side of the source material from the main parts of the detector, or (2) on the same side as the main parts of the detector, or (3) in both of these positions. Such veto counters need not measure positions, but are required only to give a signal when penetrated by a radioactive emission. Recording of data from position measuring chambers is suppressed for a short time interval after such a signal.

A detector constructed as described must be connected to a coincidence and control circuit that causes its measurements to be processed when a sequence of events occurs, as follows: (1) signals of appropriate magnitudes are observed on the position measuring electrodes of its first and second chambers within a short time interval of one another, typically less than one microsecond; (2) a sufficient signal is observed from an energy discriminating counter, if this configuration is used, within the same time interval; and (3) signals are not observed from veto counters, if these are included, within this same time interval. Such coincidence and control circuits are well known in the art. This circuit must include allowance for the response times of the detector's individual chambers and counters, if these are of different types, mechanical configurations, or operating conditions.

A detector constructed as described must also be connected to readout circuits, which convert the charge signals from its electrodes to signals proportional to coordinates, and to signal processing circuits, which convert coordinate signals obtained from readout circuits into estimated coordinates of emission origins. In one such circuit this is accomplished by multiplying the signals from a multiplicity of conductive elements of the electrode bounding a detection region by weights proportional to the positions of the elements along a coordinate lying within the plane of the electrode and normal to the orientation of the electrode elements. The circuit also sums the weighted and the unweighted signals and divides the weighted sum by the unweighted sum. This quotient is then a measure of the coordinate of the centroid of a cluster of ionization detected within a plane located within the bounded detection regions, parallel to the bounding electrodes and in a coordinate direction normal to the orientation of the conductive elements of the electrode. When the source surface is curved a correction factor must be used. Such a signal processing circuit is required for each coordinate of a source material surface for which direction measurements are to be obtained. It will combine two position measurement values obtained in its coordinate along an emission path to provide an estimated emission origin in that coordinate.

DESCRIPTION OF THE PREFERRED EMBODIMENTS

Figure 1:
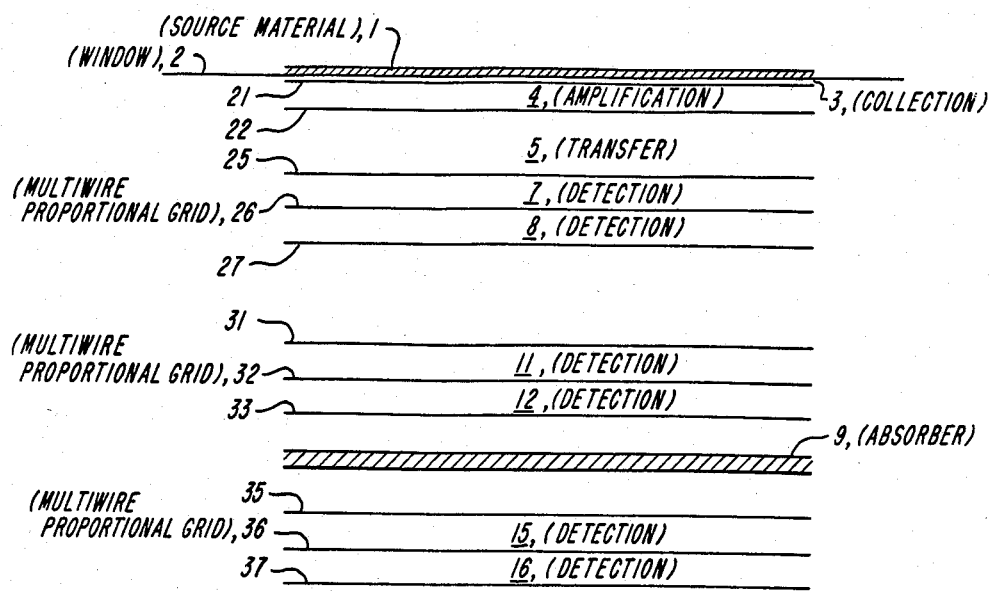
FIG. 1 is a drawing showing in cross-section the arrangement of electrodes in a planar detector which has a five-region position measuring chamber, followed by a conventional multiwire proportional chamber, followed by an optional absorber plate and another multiwire proportional chamber, and showing the position of a typical portion of source material, in accordance with this invention. This illustration is schematic only, and it does not show an enclosure, mechanical supports for electrodes, or details of construction.
Figure 3:
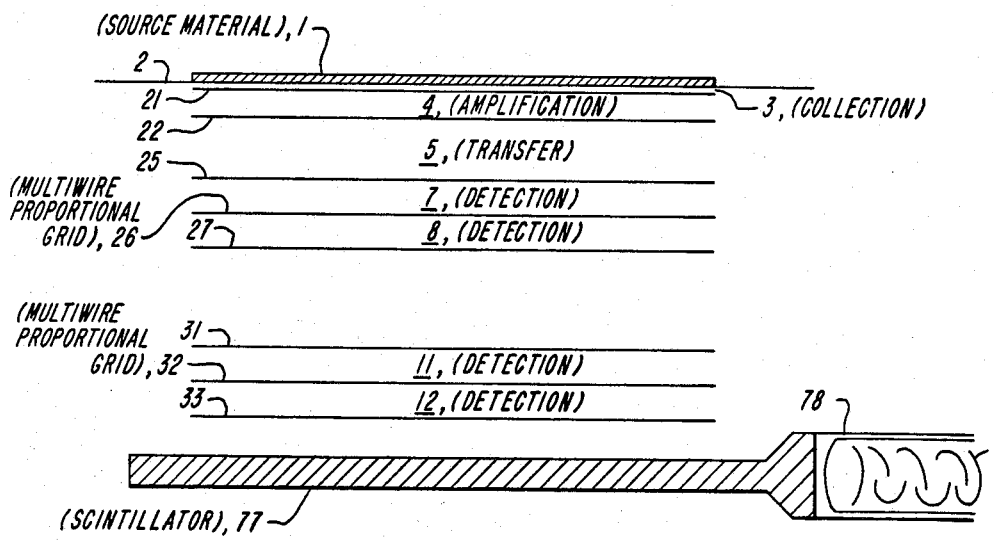
FIG. 3 is a drawing showing in cross-section the arrangement of electrodes in a planar detector which has a five-region position measuring chamber, followed by a conventional multiwire proportional chamber, followed by a scintillator plate with a phototransducer, and showing the position of a typical portion of source material, in accordance with this invention. This illustration is schematic only, and it does not show an enclosure, mechanical supports for electrodes, or details of construction.
Figure 2:
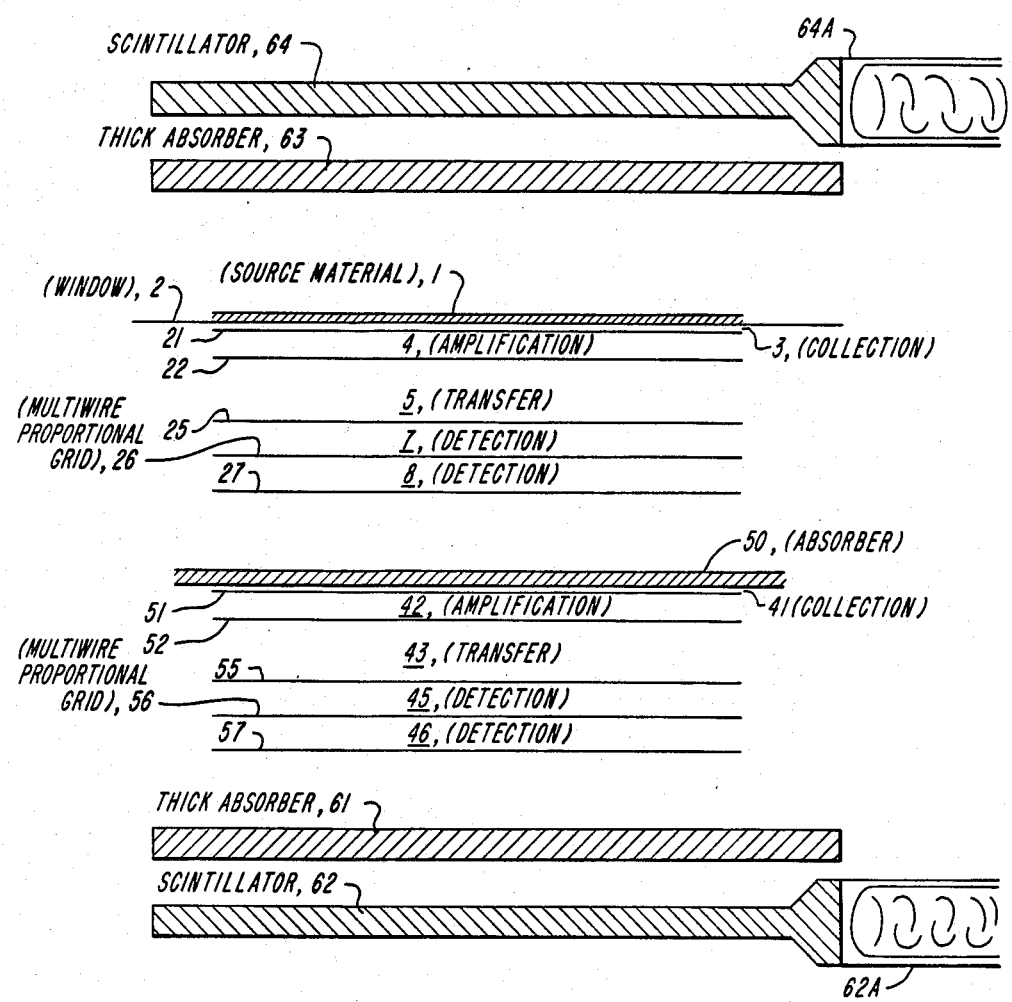
FIG. 2 is a drawing showing in cross-section the arrangement of electrodes in a planar detector which has five-region position measuring chamber, followed by an absorber plate and a second five-region position measuring chamber, and showing the position of a typical portion of source material, in accordance with this invention. This illustration is schematic only, and it does not show an enclosure, mechanical supports for electrodes, or details of construction.

FIGS. 1, 2, and 3 illustrate in cross-section three configurations for planar detector electrodes, in an apparatus designed to measure the distribution of charged particle emitting radionuclides at or near the surface of a planar source material. Each configuration includes a five-region first position measuring chamber, which measures one point on the path of a charged particle emission as close as possible to its origin, and an additional position measuring chamber, which measures a second point. This detector is particularly advantageous for energetic beta emissions, such as those from strontium-90, with a maximum emission energy of 0.54 MeV, or phosphorus-32, with a maximum energy of 1.72 MeV. The electrode planes of the detector are oriented parallel to the plane of source material and are of comparable or slightly larger dimensions. Sizes up to at least 30×50 cm are practical.

In FIG. 1, planar source material 1, carrying a distribution of charged particle emitting radionuclide, is placed immediately outside enclosure window 2, which serves as the outside electrode of collection region 3. Enclosure window 2 should be tightly stretched, thin, strong, impermeable to gases and water vapor, conductive, and low in atomic number. It can be made of coated materials, such as 50 micron polyester film with 5 micron deposited aluminum on the exterior and colloidal graphite coating on the interior. The interior of the detector, from collection region 3 through detection region 16 is filled with a gas mixture designed to provide low electron attachment and to support parallel plate amplification, such as argon with three to five percent acetone or propane. For stable operation, it is important to maintain high gas purity. Low concentrations of oxygen, water vapor, and electronegative solvents such as chlorinated hydrocarbons are required, usually below one part per million. Design estimates refer to detector operation at atmospheric pressure. For very high or low energy charged particles, spatial resolution of the detector may be improved by operation at higher or lower pressures, respectively, at a cost of more complex enclosure design.

Within the detector, enclosure window 2 and electrode planes 21, 22, 25, 26 and 27 define a five-region chamber that measures the coordinates of a point on a charged particle emission path as close as possible to the plane of source material 1. Multiwire proportional grid electrode 26 has the most positive potential; the other electrodes are at successively more negative potentials. Collection region 3 is thick enough only to provide a few primary ionization clusters along the average emission path, a thickness of about 1 mm. The electrostatic field in this region is moderate, about 50 to 100 V/mm/atm.

Electrodes 21 and 22, which bound amplification region 4, must be very tightly stretched to minimize deflection caused by mutual attraction in the strong electrostatic field of the amplification region, about 500 to 800 V/mm/atm. The thickness of amplification region 4 can be about 3 to 8 mm, with thinner regions providing more precise spatial measurements but requiring more control of dimensional uniformity. Electrodes 21 and 22 should be closely spaced wires or fibers, at a pitch not more than about a tenth the thickness of the amplification region, in order to minimize field irregularity and spatial quantization of the detector's response. The diameters of wires or fibers must be large enough so that they do not serve as corona sources, and the electrode surfaces must be as smooth as possible for the same reason. Stainless steel or beryllium copper wire, 50 to 100 microns in diameter, can be used for such electrodes. However, in order to minimize scattering of charged particle emissions, it is advantageous to use materials of low density and atomic number, such as conductively coated polyaramid fibers.

Electrodes 25 and 27 are cathodes for electrode 26, which is a multiwire proportional grid anode. The anode grid is constructed of tungsten or stainless steel wire, 20 to 30 microns in diameter, at a pitch of 1.5 to 2.5 mm. The cathodes are constructed of 50 to 150 micron diameter wire at a pitch of 1 to 3 mm. Anode to cathode spacings can be about 4 to 8 mm. Smaller spacings will enhance overall spatial resolution but will require more control of dimensional uniformity. Attainable signal amplitudes will be substantially diminished at small anode wire pitch. It will be advantageous to use cathode materials of low density and atomic number, in order to minimize scattering of charged particle emissions. Depending on anode wire diameter and pitch, electrostatic fields of about 300 to 500 V/mm/atm will be required in the detection regions.

Transfer region 5 is located between amplification region 4 and detection region 7. The thickness and electrostatic field of the transfer region will vary with design objectives. A thicker transfer region will increase isolation between the amplification and transfer regions and can improve operating stability. Additional lateral diffusion of electrons in this region can also reduce spatial quantization of detector response. However, this additional thickness will increase measurement errors from scattering. A lower electrostatic field will reduce the fraction of electrons transferred through electrode 22, increasing the isolation between amplification and transfer regions but reducing signal amplitudes, which can worsen the intrinsic precision of position measurements. Thickness of the transfer region can be about 3 to 15 mm and electrostatic field strength about 20 to 200 V/mm/atm.

The detector configuration shown in FIG. 1 has a second position measuring chamber consisting of detection regions 11 and 12, as defined by cathode electrodes 31 and 33 and multiwire proportional grid anode 32. The construction and operating characteristics are similar to those of detection regions 7 and 8. Absorber material 9 and detection regions 15 and 16 are optional. If included, detection regions 15 and 16 and electrodes 35, 36, and 37 have approximately the same construction and operating characteristics as detection regions 11 and 12 and electrodes 31, 32, and 33. It is possible to combine electrodes 27 and 31 as a single electrode; this would require obtaining positional information from electrodes 25, 26, 32, and 33.

The detector shown in FIG. 1 has at least two position measuring multiwire proportional chamber elements: electrodes 25, 26, and 27, and electrodes 31, 32, and 33. When electrons from an ionizing event reach the vicinity of a wire or fiber of multiwire proportional grid anode 26 or 32, the conditions of operation produce localized amplification near the surface of the wire. Negative electrical charge signals appear on an active anode wire, and induced positive charge signals appear on adjacent electrode elements. Divided electrodes are used for position measurement. Electrode elements for rectilinear coordinates are uniformly spaced, parallel, planar arrays of wires, connected groups of wires, or other conductive strips. Other geometries can be used for curved or nonlinear coordinates. Induced signals diminish rapidly in amplitude with distance from the anode amplification site.

Electronic readout circuits of several designs can process signals from wires or other electrode elements to obtain a positional charge centroid, locating the center of a primary cluster of ionization. The detector shown in FIG. 1 can utilize a simple but accurate method: a tapped, lumped constant, electromagnetic delay line whose taps are directly connected to the wires of a grid electrode or to small groups of such wires. The time difference between peak signals at the extremes of such a delay line is proportional to the position of the charge centroid. Another method is an analog or digital centroid circuit, in which a position weighted sum of the signals from electrode elements is divided by an unweighted sum. Each coordinate to be measured will require its own electrode elements and readout circuit.

The detector shown in FIG. 1 has optional elements consisting of absorber 9 and a multiwire proportional chamber consisting of electrodes 35, 36, and 37. These elements are included when the detector is to have a threshold emission energy for counting. The material and thickness of the absorber is chosen to stop nearly all charged particle emissions below a particular energy. It is advantageous to use a material of low atomic number, such as carbon, so that energetic x-ray fluorescence will not be produced which might be detected in some part of the apparatus. It is not necessary to provide a position measuring readout for the optional electrodes. The presence of a signal on multiwire proportional grid 36 can be taken to indicate that a charged particle emission has penetrated absorber 9.

The detector shown in FIG. 2 is an alternative configuration for the detector shown in FIG. 1, including its optional elements. This detector also has a first chamber consisting of regions 3, 4, 5, 7, and 8, as defined by window electrode 2 and other electrodes 21, 22, 25, 26, and 27, which has the same construction and characteristics as the identically numbered components of FIG. 1. Absorber 50 serves the same purpose as absorber 9 of FIG. 1. However, this absorber 50, which should either be conductive or be laminated to a conductive material, also serves as one electrode of collection region 41.

The detector in FIG. 2 has a second five-region position measuring chamber, consisting of collection region 41, amplification region 42, transfer region 43, detection regions 45 and 46, absorber electrode 50, and electrodes 51, 52, 55, 56, and 57. Except that absorber plate 50 takes the place of the window 2, this chamber has the same construction and operating characteristics as the one consisting of regions 3, 4, 5, 7, and 8, and electrodes 21, 22, 25, 26, and 27. The second detector in this configuration responds only to emissions that penetrate the absorber. For such emissions, it measures the position of ionization as close as possible to the point of emergence from the absorber, providing a second point on an emission path. The detector shown in FIG. 2 also includes additional optional elements for suppression of background radiation, consisting of either or both of scintillator plates 62 and 64 together with associated phototransducers 62a and 64a. The plates may be separated from the other elements of FIG. 2 by optional thick absorbers 61 and 63. Recording of signals from the other elements of FIG. 2 is suppressed when a signal from one or both of these scintillators is detected.

The detector shown in FIG. 3 is another alternative configuration for the detector shown in FIG. 1, including its optional elements. This detector also has a first chamber consisting of regions 3, 4, 5, 7, and 8, as defined by window electrode 2 and other electrodes 21, 22, 25, 26, and 27, which has the same construction and characteristics as the identically numbered components of FIG. 1. This detector configuration has a second position measuring chamber consisting of detection regions 11 and 12, as defined by electrodes 31, 32, and 33, which has the same construction and characteristics as the identically numbered components of FIG. 1. Scintillator plate 77 is thick enough to absorb completely any source radionuclide emission, and the signal from phototransducer 78 measures the energy of an emission. This signal can be used to reject emissions whose emission energies fall outside an acceptance range.

For the detectors of FIGS. 1 and 3, the surfaces within the detector on which two points of an emission path are measured are approximately at the center of collection region 3 and at the plane of multiwire proportional grid electrode 32. For the detector of FIG. 2, the surfaces on which two points are measured are approximately at the centers of collection regions 3 and 41. However, the effective thickness of a collection region extends into an adjacent amplification region a distance approximately equal to the thickness of the amplification region divided by the natural logarithm of the amplification gain factor for a primary electron completely traversing the amplification region.

Figure 4:
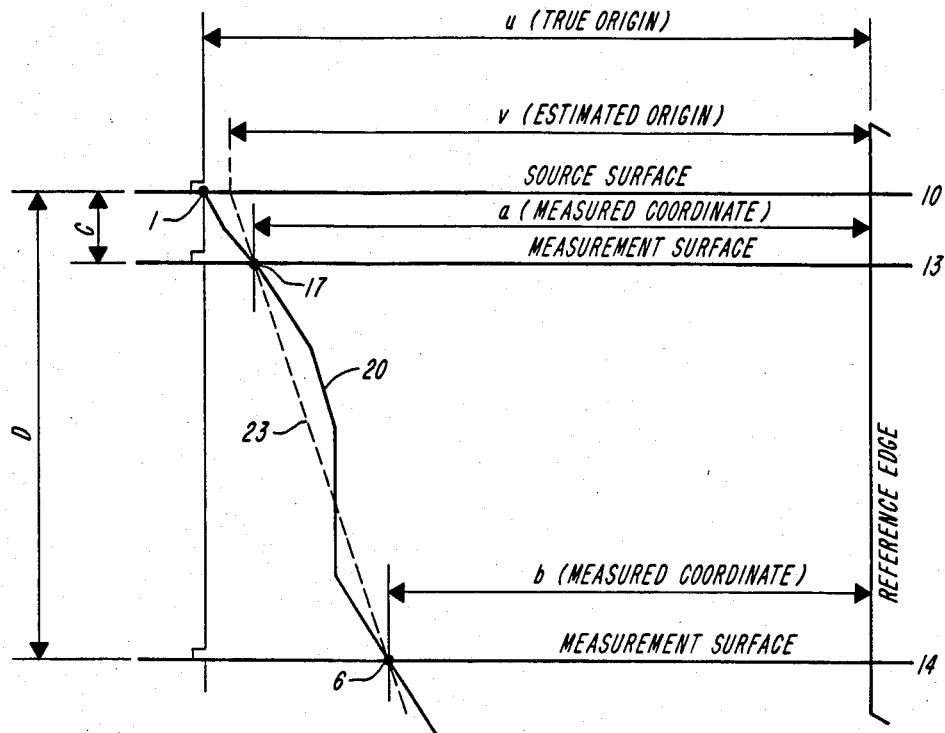
FIG. 4 is a schematic illustration, showing in cross-section a typical emission path, the measurements performed by the detector, the process of estimating an emission origin coordinate according to the principles of this invention, and the error made as a result of a scattered emission path.

FIG. 4 is a diagram of the measurement process performed by a planar detector constructed in accordance with this invention. This is a cross section in which the source material occupies plane 10 and points along a path are measured in planes 13 and 14. An emission originates at point 1, coordinate u. It follows path 20, scattering in the detector. Its path is measured at points 17 and 6, coordinates a and b (using the same reference as for u), on measurement planes 13 and 14. From these two coordinates is estimated straight line path 23, which intersects the source plane at coordinate v. Measurement planes 13 and 14 are at distances C and D along the normal from source plane 10. The formula used to adjust the measurement from point 17 and thus estimate coordinate v is:

$$v = a - (b-a)C/(D-C)$$

The above estimation may be evaluated for either or both coordinates of the source surface as each emission is recorded. It can be evaluated by dedicated signal processing circuits or by circuits included in digital data processing equipment. As shown in FIG. 4, because of scattering in the detector, there is an error (v−u) associated with this estimation, in addition to errors intrinsic to position measurement. For the specific materials and geometry of a particular detector and from well understood physical principles, it is possible to predict the distribution of estimation errors from scattering. These errors increase rapidly for emissions at large angles with respect to the normal and for emissions at low emission energies.

It is possible to improve spatial resolution, at a cost in sensitivity, by rejecting wide angle emissions, low energy emissions, or both. Absorbers 9 and 50, shown in FIGS. 1 and 2, respectively, are introduced for the purpose of filtering emissions so as to count only those above a threshold energy. The signal amplitude from phototransducer 78 of FIG. 3 can also be used to create a similar energy threshold. The value of a measured coordinate difference, (b−a) as shown in FIG. 4, is proportional to the tangent of the projected path angle with respect to the normal. When the source surface is curved the quantity should be multiplied by a suitable correction factor according to the specific geometry of the curved surface. Such a quantity can be compared with a limiting value to reject wide angle emissions.

Figure 5:
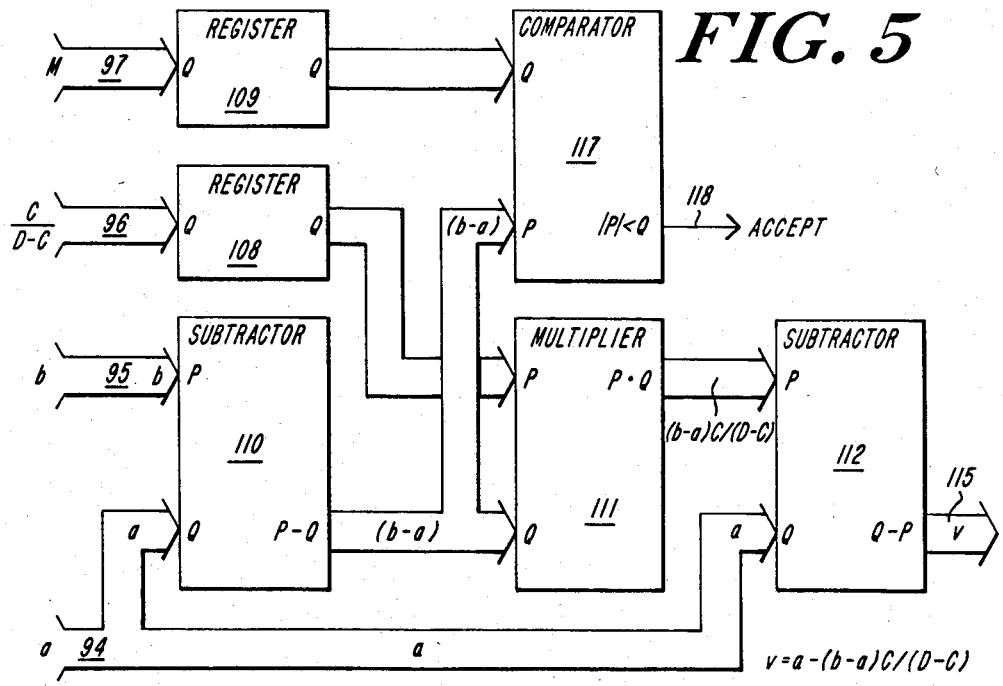
FIG. 5 is a block diagram of a signal processing circuit that will perform the calculation required to estimate emission origin coordinates in accordance with this invention.

FIG. 5 gives a block diagram of an electronic circuit that will implement the coordinate estimation and path angle threshold performed according to the process of this invention. This circuit performs such a procedure for one coordinate. Digital position measurements required as input to this circuit may be produced by either the readout circuit illustrated in FIG. 5B or that shown in FIG. 5C.

Figure 5B:
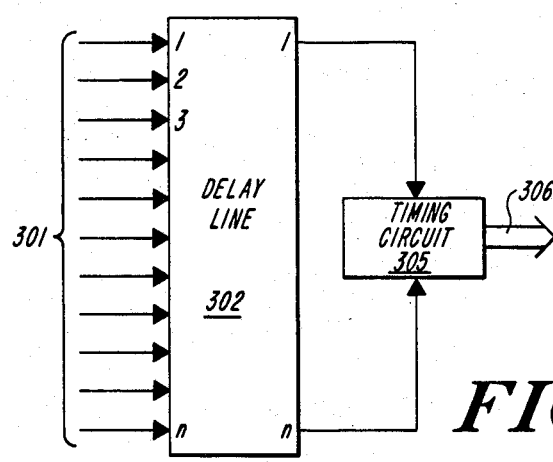
FIGS. 5B and 5C show in block diagram form readout circuits suitable for use in conjunction with the circuit of FIG. 5.

FIG. 5B shows a readout circuit for one coordinate from one position measuring chamber, based on a tapped, lumped constant delay line. The separate conductive elements of a planar electrode are directly connected as inputs 301 to delay line 302. The ends of this delay line are connected to timing circuit 305. The timing circuit 305 output 306 is a position measurement signal.

Figure 5C:
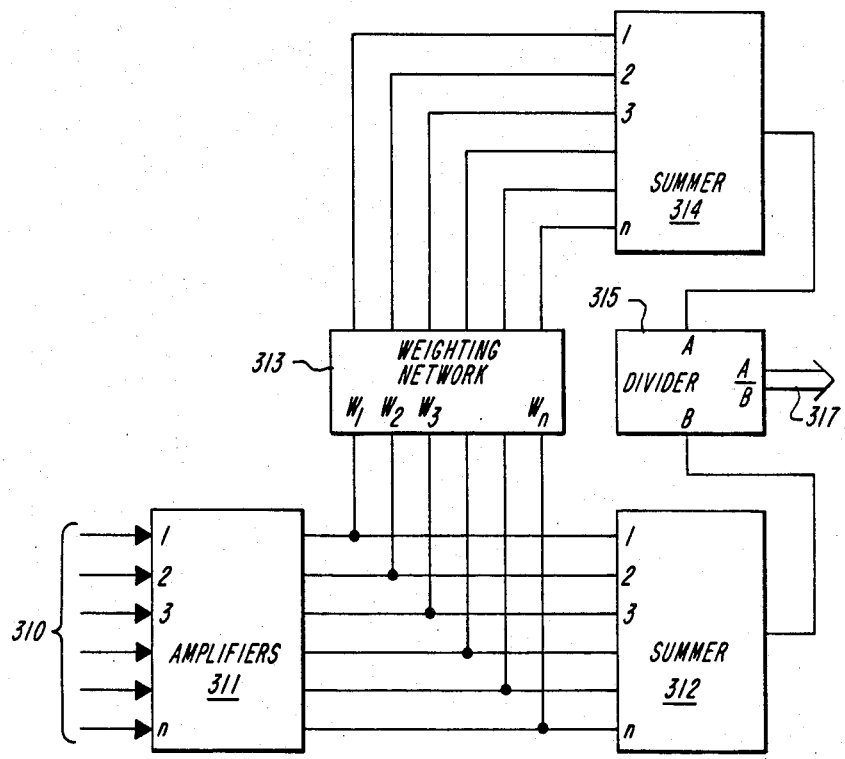

FIG. 5C shows a readout circuit for one coordinate from one position measuring chamber, based on an analog centroid calculation. The separate conductive elements of a planar electrode element are connected as inputs 310 to a bank of amplifiers 311. The amplifier outputs are sent directly to a summer 312, which produces as its output an unweighted sum, and through weighting network 313 to another summer 314, which produces as its output a weighted sum, where each signal is weighted proportionally to the position of the conductive element which produced it. Divider 315 obtains the quotient of the weighted sum divided by the unweighted sum. Output 317 provides a signal proportional to the positional centroid. It requires position measurements a and b on inputs 94 and 95, corresponding to measurements a and b as illustrated in FIG. 4. Input 96 is provided for a constant whose value is proportional to C/(D−C), as these distances are illustrated in FIG. 4. The value of this constant is retained in register 108.

Subtractor 110 of FIG. 5 accepts a and b as inputs and produces their difference (b−a) as output. Multiplier 111 accepts as input the difference (b−a) and the constant proportional to C/(D−C) and produces an output their product. Subtractor 112 accepts as input this product and measurement a; it produces their difference as output 115. This output is proportional to the estimated emission origin coordinate v as shown in FIG. 4.

Difference (b−a) from the output of subtractor 110 of FIG. 5 is also used as one input to comparator 117. The other comparator input comes from register 109, which retains a value from input 97 corresponding to the value of (b−a) at or above which emission paths are at too large an angle with respect to the normal to be accepted. Comparator 117 produces a signal on output 118 when the difference (b−a) is less than this limiting value. This is intended to signal acceptance of the associated projected angle.

The circuit of FIG. 5 can be implemented using digital integrated circuits with static, clocked, or programmable operation. For such an implementation, measurements a and b, constant C/(D−C), and the angle limiting value must be digitized and presented in an encoded representation. It is also possible to implement an equivalent analog circuit. For analog implementation, the inputs must be presented as analog voltages or currents.

Figure 6:
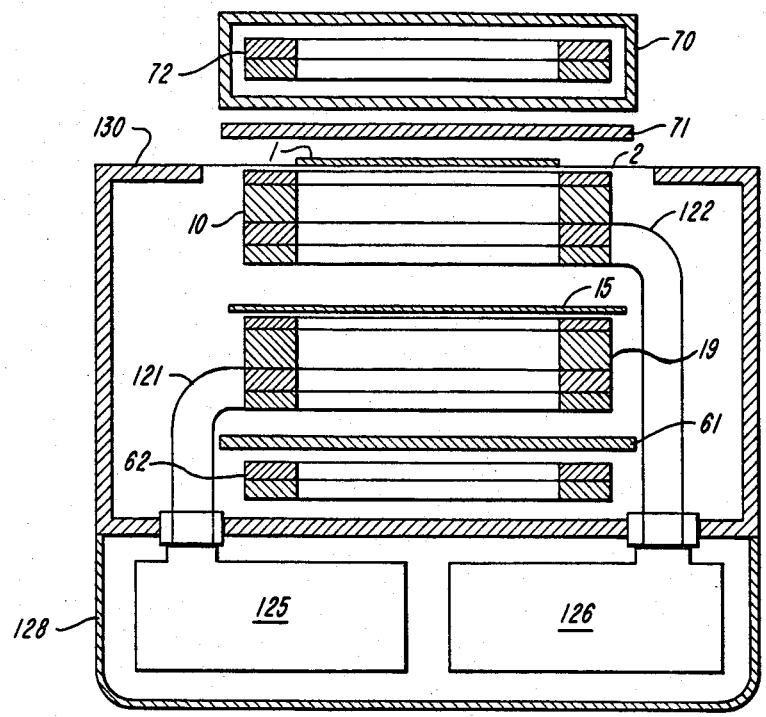
FIG. 6 is a drawing showing in cross-section the arrangement of elements of an apparatus incorporating a detector as shown in FIG. 2, within an enclosure, with optional veto counters both inside and outside the enclosure, and showing the position of a typical plane of source material, in accordance with this invention. This drawing does not show details of construction.

FIG. 6 shows one configuration for a complete detector, including an enclosure, readout circuits, and optional veto counters. Source material 1 is placed over window 2 of main enclosure 130. Within this are chambers in the configuration of FIG. 2, a five-region chamber 10 followed by absorber plate 15 and second five-region chamber 19. Signal cables 121 and 122 carry signals from the position measurement electrodes of the chambers through the rear wall of the detector to electronic readout circuits 125 and 126, located within rear enclosure 128.

Within main enclosure 130 of FIG. 6, following the position measuring chambers, are optional thick absorber 61 and multiwire proportional chamber 62, which is of the type shown in FIG. 1 by electrodes 35, 36, and 37. The optional absorber 61 is thick enough to stop any emission from the source material, and chamber 62 therefore responds only to cosmic rays or other background radiation. On the opposite side of source material 1 from the detector is optional separate enclosure 70, thick absorber 71, and multiwire proportional chamber 72, which is of the same type as multiwire proportional chamber 62. This chamber also responds only to background radiation. The function of the two optional counters is to provide veto signals for cosmic rays and other background radiation. Signals from the position measuring chambers of detector which occur within a short time of such veto signals are ignored. Veto counters make it possible to record extremely weak source distributions without background from most radioactive emissions of natural origin.

Figure 7:
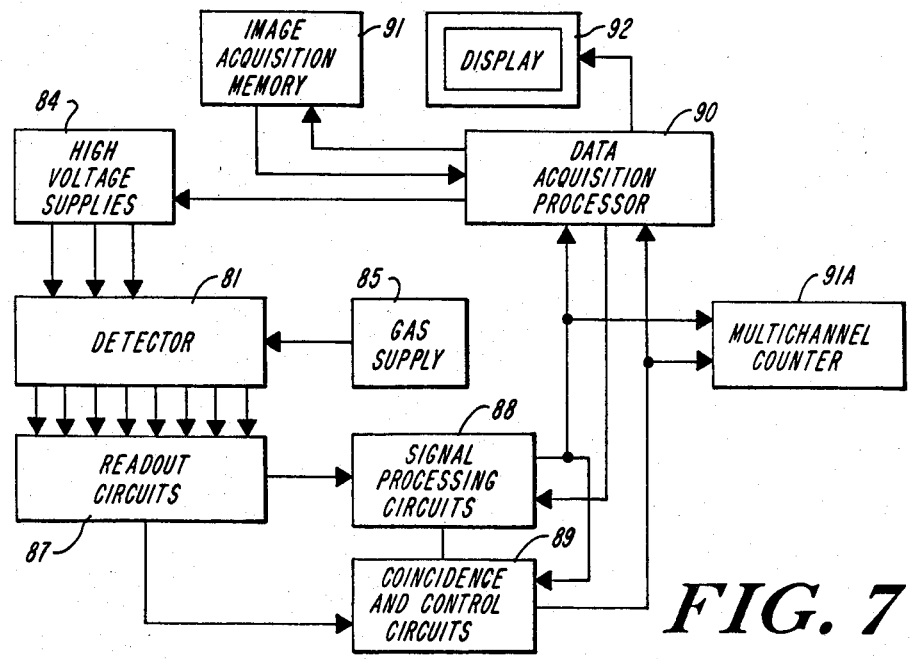
FIG. 7 is a block diagram showing the major elements of a data acquisition system incorporating a detector and signal processing circuit constructed in accordance with this invention.

FIG. 7 shows the major elements of a data acquisition system incorporating the apparatus and process of this invention. Detector 81, constructed as shown in FIGS. 1, 2, or 3 and FIG. 6, is connected to high voltage supplies 84 and to gas supply 85 to establish its operating conditions. Readout circuits 87 process charge signals from position measuring chamber elements to produce signals proportional to measured ionization coordinates. Positional measurements are inputs to signal processing circuits 88, as shown in FIG. 5, for each coordinate of estimated emission origins from the surface of the source material. The coordinate outputs of signal processing circuits 88, the signals from other detection elements, and the angle comparison outputs of the signal processing circuits 88, are inputs for coincidence and control circuit 89, which triggers data processor 90 to read estimated emission origin coordinates from signal processing circuits 88 when both associated path angles are within acceptance limits. Data acquisition processor 90 is typically a digital circuit.

The data acquisition processor 90 may be arranged to read signals from the position measuring chambers and govern the chambers' operation by regulating the electrode voltages. It also sets the predetermined signal levels, predetermined time intervals, limiting value associated with wide angle emissions and the predetermined range of emission energies in signal processing circuits 88. Data processor 90 accumulates accepted counts in data acquisition memory 91, which may also take the form of a multichannel digital counter 91a, or any other conventional memory device. Data processor 90 also records and analyzes estimated origin coordinates of emissions from the source material surface and presents the results of its analysis on display 92. Such display may be in the form of a map or image of the coordinates constructed by the data processor 90.

What is claimed is:

1. An apparatus for measuring a two-dimensional distribution of a charged particle emitting radionuclide at or near the surface of a planar source material, comprising:
    (a) a gas confining enclosure with a thin wall, or window, positioned adjacent to said source material and formed of a composition and thickness that allows charged particle emissions impinging thereon to penetrate it with minimal absorption and scattering;
    (b) a first position measuring chamber located inside said enclosure and oriented so as to provide a first position measurement in two coordinates within a first plane parallel to the source material of an ionization signal produced by a charged particle emission passing through said first plane, said chamber configured so as to locate said first plane close to the plane of said source material;
    (c) a second position measuring chamber located inside said enclosure and displaced away from said enclosure window, oriented so as to provide a second position measurement in two coordinates within a second plane parallel to said source material of an ionization signal produced by a charged particle emission passing through said second plane; and
    (d) circuitry means for comparing the measured positions of ionization signals occurring during a predetermined time period in said first and second position measuring chambers, calculating the coordinates at which a straight line passing through said measured positions intersects the plane of said source material, said location being identified as the estimated origin of an emission, and determining whether the differences in said measured positions exceed limiting values associated with an estimated path at maximum projected angles with respect to said first and second planes.

2. An apparatus constructed in accordance with claim 1 wherein the dimensions of said first and second position measuring chambers are substantially coextensive with the surface dimensions of said source material.

3. An apparatus in accordance with claim 1 wherein each position measuring chamber is a multiwire gas proportional detector, said multiwire gas proportional chamber consisting of two detection regions, each a gas volume, bounded and separated from one another by planar electrodes, each oriented substantially parallel to the surface of said source material, with the electrode separating said detection regions constructed as a grid of fine wires or conductive fibers, within which detection regions a strong electrostatic field provided by said planar electrodes moves primary ionization electrons toward the fine wire or fiber grid and creates in the vicinity of its wires or fibers secondary multiplication of electrons, one or two of the said planar electrodes bounding said detection regions providing position dependent charge signals, from which readout circuitry measures centroids of ionization in one or two coordinates of the plane of said fine wire or fiber grid.

4. An apparatus constructed in accordance with claim 1 wherein said first position measuring chamber utilizes proportional amplification of ionization in a gas and includes regions of gas volume in the following sequence, moving away from said source material, which are bounded and separated from one another by planar electrodes, each oriented substantially parallel to the surface of said source material, with each electrode separating two of said regions of gas volume constructed as a mesh or grid so as to permit the transfer of electrons from one region to another:
    (a) a collection region, nearest to said source material, for collecting primary ionization electrons from a short segment of the track of a charged particle emission close to the surface of said source material, within which collection region an electrostatic field provided by the planar electrodes bounding the collection region moves said primary electrons away from said source material;
    (b) an amplification region, next following said collection region, for providing multiplication of primary electrons collected in said collection region within which amplification region a strong electrostatic field provided by the planar electrodes bounding the amplification region moves electrons away from said source material and induces throughout the volume of gas in said region, secondary multiplication of electrons at a substantially constant amplification factor per unit thickness traversed by electrons within said region;

(c) a transfer region, next following said amplification region, for isolating said amplification region from subsequent regions, within which transfer region an electrostatic field provided by the planar electrodes bounding the transfer region moves electrons away from said source material; and (d) two detection regions, next following said transfer region, for detecting and measuring positions of ionization, with a planar electrode dividing said detection regions that consists of a grid of fine wires or conductive fibers, within which detection regions a strong electrostatic field provided by the planar electrodes bounding and separating the detection regions moves electrons toward the fine wire of fiber grid and creates in the vicinity of its wires or fibers additional secondary multiplication of electrons, two of said planar electrodes bounding said detection regions providing position dependent charge signals, from which readout circuitry measures centroids of ionization in two coordinates of the plane of said fine wire or fiber grid.

5. An apparatus constructed in accordance with claim 1 wherein said second position measuring chamber consists of two detection regions, bounded and separated from one another by planar electrodes, each oriented substantially parallel to the surface of said source material, with the electrode separating said detection regions constructed as a grid of fine wires or conductive fibers, within which detection regions a strong electrostatic field provided by said planar electrodes moves primary ionization electrons toward the fine wire or fiber grid and creates in the vicinity of its wires or fibers secondary multiplication of electrons, one or two of said planar electrodes of said detection regions providing position dependent charge signals, from which readout circuitry measures centroids of ionization in one or two coordinates of the plate of said fine wire or fiber grid.

6. An apparatus in accordance with claim 5 wherein said second position measuring chamber is followed by an absorber plate and a third ionization sensitive chamber, the composition and thickness of said absorber plate being chosen to absorb charged particle emissions having emission energies below a predetermined threshold, while transmitting a substantial portion of charged particle emissions at emission energies higher than said threshold, said third ionization sensitive chamber consisting of two detection regions, bounded and separated from one another by planar electrodes, each oriented substantially parallel to the surface of said source material, with the electrode separating said detection regions constructed as a grid of fine wires or conductive fibers, within which detection regions a strong electrostatic field provided by said planar electrodes moves primary ionization electrons toward the fine wire or fiber grid and creates in the vicinity of its wires or fibers secondary multiplication of electrons, one of said planar electrodes of said detection regions providing charge signals, from which readout circuitry determines the presence of a charged particle emission that has penetrated said absorber plate.

7. An apparatus in accordance with claim 6 wherein a controller causes information from said first and second position measuring chambers to be recorded when signals from said position measuring chambers rise above predetermined levels within a predetermined time interval, when said measured positions do not exceed limiting values associated with an estimated emission path at maximum angles, and when signals from said third ionization sensitive chamber indicate an emission with an energy within a predetermined range.

8. An apparatus in accordance with claim 7 having a data acquisition processor means connected to said position measuring chambers and to said controller for reading signals from said position measuring chambers and for governing the operations of said position measuring chambers by regulating the electrode voltages of said position measuring chambers and by setting said predetermined signal levels, said predetermined time interval, said limiting values associated with an estimated emission path at maximum projected angles and said predetermined range of emission energies, and for constructing, recording, analyzing, or displaying a map or image of said coordinates of radioactive emissions from said source material surface.

9. An apparatus constructed in accordance with claim 1 or 5 wherein said second position measuring chamber is followed by a plate of solid scintillator material, constructed with such composition and thickness as to absorb a charged particle emission of any energy produced by a source radionuclide, and producing a light signal when activated by ionizing radiation, which is converted by means of a phototransducer to an electrical signal from the amplitude of which readout circuitry determines the energy of a charged particle emission that has been absorbed by said scintillator plate, for the purpose of accepting only emissions at energies within a predetermined range.

10. An apparatus in accordance with claim 9 wherein a controller causes information from said first and second position measuring chambers to be recorded when signals from said position measuring chambers rise above predetermined levels within a predetermined time interval, when said measured positions do not exceed limiting values associated with an estimated emission path at maximum angles, and when signals from said phototransducer indicate an emission with an energy within a predetermined range.

11. An apparatus in accordance with claim 10 having a data acquisition processor means connected to said position measuring chambers and to said controller for reading signals from said position measuring chambers and for governing the operations of said position measuring chambers by regulating the electrode voltages of said position measuring chambers and by setting said predetermined signal levels, said predetermined time interval, said limiting values associated with an estimated emission path at maximum projected angles and said predetermined range of emission energies, and for constructing, recording, analyzing, or displaying a map or image of said coordinates of radioactive emissions from said source material surface.

12. An apparatus constructed in accordance with any of the claims 1, 3 or 4 wherein said second position measuring chamber is immediately preceded by an absorber plate, the composition and thickness of said absorber plate being chosen to absorb charged particle emissions having emission energies below a predetermined threshold; while transmitting a substantial portion of charged particle emissions at emission energies higher than said threshold, and wherein said second position measuring chamber utilizes proportional amplification of ionization in a gas and includes regions of gas volume in the following sequence, moving away from said source material, which are bounded and separated from one another by planar electrodes, each oriented substantially parallel to the surface of said source material, with each electrode separating two of said regions of gas volume constructed as a mesh or grid so as to permit the transfer of electrons from one region to another:

(a) a collection region, nearest to said source material, for collecting primary ionization electrons from a short segment of the track of a charged particle emission close to the surface of said source material, within which collection region an electrostatic field provided by the planar electrodes bounding the collection region moves said primary electrons away from said source material, said collection region utilizing said absorber plate as a planar electrode on the side toward said source material surface;

(b) an amplification region, next following said collection region, for providing multiplication of primary electrons collected in said collection region, within which amplification region a strong electrostatic field provided by the planar electrodes bounding the amplification region moves electrons away from said source material and induces throughout the volume of gas in said region secondary multiplication of electrons, at a substantially constant amplification factor per unit thickness traversed by electrons within said region;

(c) a transfer region, next following said amplification region, for isolating said amplification region from subsequent regions, within which transfer region an electrostatic field provided by the planar electrodes bounding the transfer region moves electrons away from said source material; and (d) two detection regions, next following said transfer region, for detecting and measuring positions of ionization, with a planar electrode dividing said detection regions that consists of a grid of fine wires or conductive fibers, within which detection regions a strong electrostatic field provided by the planar electrodes bounding the detection regions moves electrons toward the fine wire or fiber grid and creates in the vicinity of its wire or fibers additional secondary multiplication of electrons, one or two of the planar electrodes bounding the said detection regions providing position dependent charge signals, from which readout circuitry measures centroids of ionization in one or two coordinates of the plane of said fine wire or fiber grid.

13. An apparatus constructed in accordance with claim 12, employing for either or both dimensions of said second position measuring chamber a readout circuit that obtains a charge centroid in one dimension, consisting of a tapped, lumped constant, electromagnetic delay line whose taps are directly connected to conductive elements of an electrode bounding a detection region, together with electronic timing circuits that measure the time difference between peak signals at the extremes of said delay line, said time difference being a measure of the coordinate of the centroid of a cluster of detected ionization within a plane located in said detection region, parallel to the electrodes bounding said detection region, and in a coordinate direction normal to the orientation of said conductive elements.

14. An apparatus constructed in accordance with claim 12, employing for either or both dimensions of said second position measuring chamber readout circuit means for obtaining a charge centroid in one dimension, by multiplying the signals from a multiplicity of conductive elements of an electrode bounding a detection region by weights proportional to the positions of said elements along a coordinate within the plane of said electrode and normal to the orientation of its elements, summing the weighted signals, summing the unweighted signals, and dividing the weighted sum by the unweighted sum, the output from division being a measure of the coordinate of the centroid of a cluster of detected ionization within a plane located in said detection region, parallel to the electrodes bounding said detection region, and in a coordinate direction normal to the orientation of said conductive elements.

15. An apparatus constructed in accordance with any of the claims 1, 3, 4, or 5, employing for either or both dimensions of any of said position measuring chambers a readout circuit that obtains a charge centroid in one dimension, consisting of a tapped, lumped constant, electromagnetic delay line whose taps are directly connected to conductive elements of an electrode bounding a detection region, together with electronic timing circuit means for measuring the time difference between peak signals at the extremes of said delay line, said time difference being a measure of the coordinate of the centroid of a cluster of detected ionization within a plane located in said detection region, parallel to the electrodes bounding said detection region, and in a coordinate direction normal to the orientation of said conductive elements.

16. An apparatus constructed in accordance with any of the claims 1, 3, 4, or 5, employing for either or both dimensions of any of said position measuring chambers a readout circuitry means for obtaining a charge centroid in one dimension, by, multiplying the signals from a multiplicity of conductive elements of an electrode bounding a detection region by weights proportional to the positions of said elements along a coordinate within the plane of said electrode and normal to the orientation of its elements, summing the weighted signals, summing the unweighted signals, and dividing the weighted sum by the unweighted sum, the output from division being a measure of the coordinate of the centroid of a cluster of detected ionization within a plane located in said detection region, parallel to the electrodes bounding said detection region, and in a coordinate direction normal to the orientation of said conductive elements.

17. An improvement to an apparatus in accordance with claim 1 wherein one or more multiwire counters employing proportional amplification of ionization in a gas are placed adjacent to said source material on the side away from said position measuring chambers or adjacent to said second position measuring chamber on the side away from said source material, said multiwire counter or counters covering an area substantially coextensive with or larger than said source material surface and having an orientation substantially parallel thereto, signals from said multiwire counter or counters indicating the occurrence of background radiation events and inhibiting recording of signals from said first and second position measuring chambers during said events.

18. An improvement to an apparatus in accordance with claim 17 and providing further that said multiwire counter includes an absorber plate of such composition and thickness as to stop all charged particle emissions from said source material, said absorber plate being located on the side of said multiwire counter toward said source material.

19. An improvement to an apparatus in accordance with claim 1 wherein one or more scintillation counters are placed adjacent to said source material on the side away from said position measuring chambers or adjacent to said second position measuring chamber on the side away from said source material, said scintillation counter consisting of a plate of solid scintillator material producing a light signal, when activated by radiation, which is converted to an electrical signal by a phototransducer, said scintillation counter or counters covering an area substantially coextensive with or larger than said source material surface and having an orientation substantially parallel thereto, signals from said scintillation counter or counters indicating the occurrence of background radiation events and inhibiting recording of signals from said first and second position measuring chambers during said events.

20. An improvement to an apparatus in accordance with claim 19 and providing further that said scintillation counter includes an absorber plate of such composition and thickness as to stop all charged particle emissions from said source material, said absorber plate located on the side of said scintillation counter toward said source material.

21. An apparatus in accordance with claim 1 wherein a controller causes information from said first and second position measuring chambers to be recorded when signals from said position measuring chambers rise above predetermined levels within a predetermined time interval and when said measured positions do not exceed limiting values associated with an estimated emission path at maximum angles.

22. An apparatus in accordance with claim 21 having a data acquisition processor means connected to said position measuring chambers and to said controller for reading signals from said position measuring chambers and for governing the operations of said position measuring chambers by regulating the electrode voltages of said position measuring chambers and by setting said predetermined signal levels, said predetermined time interval, and said limiting values associated with an estimated emission path at maximum projected angles, and for constructing, recording, analyzing or displaying a map or image of said coordinates of radioactive emissions from said source material surface.

23. A measurement process for obtaining the locations of charged particle emitting radionuclides at or near the planar or curved surface of a source material to be mapped, comprising the steps of:
(a) measuring the centroid of ionization for a short segment of an emission path close to the emission origin using a first ionization detection element having a sensitive area substantially parallel to and coextensive with the area of the surface to be mapped;
(b) measuring the centroids of ionization for short segments of an emission path displaced away from the emission origin using one or more additional ionization detection element having a sensitive area substantially parallel to and coextensive with the area of the surface to be mapped; and
(c) estimating the origin and direction of a charged particle emission using a means for correlating the coordinates obtained from said ionization detection elements.

24. A measurement process in accordance with claim 23 wherein said means for correlating coordinates obtained from said ionization detection elements determines for one or both dimensions of the source material surface the differences between position measurements obtained in such a dimension from said first and subsequent ionization detection elements, and, based on said position differences and the distances between said surface to be mapped and the measuring surfaces of said detection elements, determines for said dimension at least one of the following:
(a) the estimated emission origin coordinate, by means of a line of sight passing through the positions obtained from said position measurements, being the coordinate obtained from said first ionization detection element less the difference in coordinates obtained from said first and subsequent ionization detection elements multiplied by a distance ratio, said distance ratio being the distance between said surface to be mapped and the measuring surface of said first detection element divided by the distance between the measuring surfaces of said first and subsequent detection elements, multiplied by a correction factor for other than planar surfaces; and
(b) the tangent of the estimated projected emission angle, by means of a line of sight passing through the positions obtained from said position measurements, being the ratio of said coordinate difference to the distance between the measuring surfaces of said first and subsequent ionization detection elements, or a quantity proportional thereto, multiplied by a correction factor for other than planar surfaces, for the purpose of regulating the counting of emissions according to a range of acceptable emission angles.

25. A measurement process in accordance with claim 23 and further utilizing an absorber of such composition and thickness as to inhibit the passage of charged particle emissions from said surface to be mapped when the emission energy is below a predetermined limiting value, said absorber having an area substantially parallel to and coextensive with said area of the surface to be mapped, displaced away from said surfaces to be mapped, and located between two of said ionization detection elements, to be used for restricting counting of emissions to those emissions for which ionization is detected by the ionization detection element on the side of said absorber away from said surface to be mapped.

26. A measurement process in accordance with claim 25 utilizing a controller which causes information from said ionization detection elements to be recorded when signals from said ionization detection elements rise above predetermined levels within a predetermined time interval, when said direction of a charged particle emission does not exceed limiting angle values associated with an estimated emission path at maximum angles, and when signals from the said ionization detection element farthest from said source material indicate an emission with an energy within a predetermined range.

27. A measurement process in accordance with claim 23 and further utilizing an energy measuring ionization detection element of such composition and thickness as to fully absorb and quantify the energy of a charged particle emission at any energy produced by a source radionuclide on said surface, said detection element having a sensitive area substantially parallel to and coextensive with the area of the surface to be mapped and displaced further away from said surface to be mapped than any of the ionization detection elements described in claim 23, for the purpose of regulating the counting of emissions according to a range of acceptable emission energies.

28. A measurement process in accordance with claim 27 utilizing a controller which causes information from said ionization detection elements to be recorded when signals from said ionization detection elements rise above predetermined levels within a predetermined time interval, when said direction of a charged particle emission does not exceed limiting angle values associated with an estimated emission path at maximum angles, and when signals from said energy measuring ionization detection element indicate an emission with an energy within a predetermined range.

29. A measurement process in accordance with claims 26 or 28 utilizing a data acquisition processor which is connected to said ionization detection elements and to said controller, which data acquisition processor reads signals from said ionization detection elements and governs the operations of said ionization detection elements by regulating the electrode voltages of said ionization detection elements and by setting said predetermined signal levels, said predetermined time interval, said limiting angle values associated with an estimated emission path at maximum projected angles, and said predetermined range of emission energies, and which data acquisition processor constructs, records, analyzes, or displays a map or image of said estimated origins of charged particle emissions from said source material surface.

30. A measurement process for acquiring in accordance with any of the claims 23, 24, 25 or 27, a digital image of the distribution of radionuclides on said surface to be mapped, utilizing a multichannel digital counter or memory array, implemented with or without control by a digital processing system, which associates with each area element of said surface to be mapped a count that is incremented for each emission recorded by said ionization detection elements for which emission angles, if determined in accordance with claim 24, are within said range of acceptable emission angles, and for which emission energies, if limited in accordance with claim 25 or measured in accordance with claim 27, are within said range of acceptable emission energies, and for which estimated emission origin coordinates fall within the spatial boundaries of said area element.

31. A measurement process in accordance with claim 23 utilizing a multiwire gas proportional chamber for any of said ionization detection elements, said multiwire gas proportional chamber consisting of two detection regions, each a gas volume, bounded and separated from one another by electrodes which span a curved or planar surface, each oriented substantially parallel to the surface of said source material, with the separating electrode constructed as a grid of fine wires or conductive fibers, within which detection regions a strong electrostatic field provided by said electrodes moves primary ionization electrons toward the fine wire or fiber grid and creates in the vicinity of its wires or fibers secondary multiplication of electrons, one of the said electrodes of said detection regions providing position dependent charge signals, from which readout circuitry measures centroids of ionization in one coordinate of the surface of said fine wire or fiber grid.

32. A measurement process in accordance with claim 31 wherein said multiwire gas proportional chamber is utilized together with an amplification region, for providing multiplication of primary electrons entering from the side of said amplification region toward said source material, said amplification region consisting of a gas volume bounded by electrodes which span a curved or planar surface, each oriented substantially parallel to the surface of said source material, within which amplification region a strong electrostatic field provided by said electrodes moves electrons away from said source material and induces throughout the volume of gas in said region secondary multiplication of electrons at a substantially constant amplification factor per unit thickness traversed by electrons within said region, with the electrode bounding said amplification region on the side away from said source material, toward said multiwire gas proportional chamber, and the electrode bounding said multiwire proportional chamber on the side toward said amplification region constructed as a mesh or grid, in order to permit the transfer of electrons from said amplification region into said multiwire proportional chamber.

33. A measurement process in accordance with claim 32 wherein said multiwire proportional chamber and said amplification region are utilized together with a transfer region, in order to isolate said multiwire proportional chamber from said amplification region, said transfer region consisting of a gas volume defined and bounded by the nearest electrode bounding said amplification region and bounding said multiwire proportional chamber, within which transfer region an electrostatic field that is provided by the electrodes bounding said transfer region and that is significantly weaker than the field of said amplification region moves electrons away from said amplification region toward said multiwire proportional chamber.

34. A measurement process in accordance with claim 32 wherein said amplification region is utilized together with a collection region on the side of said amplification region toward said source material, in order to collect primary ionization electrons from a short segment of the track of a charged particle emission close to the surface of said source material, said collection region consisting of a gas volume defined and bounded by an electrode, on the side toward said source material, and by the nearest electrode bounding said amplification region, within which collection region an electrostatic field that is provided by said electrodes bounding said collection region and that is significantly weaker than the field of said amplification region moves electrons away from said source material toward said amplification region, with said nearest electrode bounding said amplification region constructed as a mesh or grid, in order to permit the transfer of electrons from said collection region into said amplification region.

35. An improvement to a measurement process in accordance with claim 23 utilizing one or more multiwire counters employing proportional amplification of ionization in a gas that are placed adjacent to said source material on the side away from said ionization detection elements or adjacent to the last of said ionization detection elements on the side away from said source material, said multiwire counter or counters covering an area substantially coextensive with or larger than said source material surface and having an orientation substantially parallel thereto, signals from said multiwire counter or counters indicating the occurrence of background radiation events and inhibiting recording of signals from said ionization detection elements during said events.

36. An improvement to a measurement process in accordance with claim 35 and providing further that said multiwire counter includes an absorber plate of such composition and thickness as to stop all charged particle emissions from said source material, said absorber plate located on the side of said multiwire counter toward said source material.

37. An improvement to a measurement process in accordance with claim 23 utilizing one or more scintillation counters that are placed adjacent to said source material on the side away from said ionization detection elements or adjacent to the last of said ionization detection elements on the side away from said source material, said scintillation counter consisting of a plate of solid scintillator material producing a light signal, when activated by radiation, which is converted to an electrical signal by a phototransducer, said scintillation counter or counters covering an area substantially coextensive with or larger than said source material surface and having an orientation substantially parallel thereto, signals from said scintillation counter or counters indicating the occurrence of background radiation events and inhibiting recording of signals from said ionization detection elements during said events.

38. An improvement to a measurement process in accordance with claim 37 and providing further that said scintillation counter includes an absorber plate of such composition and thickness as to stop all charged particle emissions from said source material, said absorber plate located on the side of said scintillation counter toward said source material.

39. A measurement process in accordance with claim 23 utilizing a controller which causes information from said ionization detection elements to be recorded when signals from said ionization detection elements rise above predetermined levels within a predetermined time interval and when said direction of a charged particle emission does not exceed limiting angle values associated with an estimated emission path at maximum angles.

40. A measurement process in accordance with claim 39 utilizing a data acquisition processor which is connected to said ionization detection elements and to said controller, which data acquisition processor reads signals from said ionization detection elements and governs the operations of said ionization detection elements by regulating the electrode voltages of said ionization detection elements and by setting said predetermined signal levels, said predetermined time interval, and said limiting angle values associated with an estimated emission path at maximum projected angles, and which data acquisition processor constructs, records, analyzes, or displays a map or image of said estimated origins of charged particle emissions from said source material surface.

* * * * *

UNITED STATES PATENT AND TRADEMARK OFFICE
CERTIFICATE OF CORRECTION

PATENT NO. : 4,670,656
DATED : June 2, 1987
INVENTOR(S) : Craig Bolon

It is certified that error appears in the above-identified patent and that said Letters Patent are hereby corrected as shown below:

Column 14, line 29 "an" should be --as--;

Column 17, line 44 "plate" should be --plane--;

Column 19, line 49 "wire" should be --wires--;

Column 21, line 47 after "angles" insert --and said predetermined range of emission energies--.

Signed and Sealed this

Twenty-sixth Day of January, 1988

Attest:

DONALD J. QUIGG

Attesting Officer     Commissioner of Patents and Trademarks